US008099146B1

(12) United States Patent  
Koh

(10) Patent No.: US 8,099,146 B1  
(45) Date of Patent: Jan. 17, 2012

(54) SYSTEM AND METHOD FOR CALIBRATING A BLOOD OXYGEN SATURATION SENSOR FOR USE WITH AN IMPLANTABLE MEDICAL DEVICE

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 1700 days.

(21) Appl. No.: 11/387,579

(22) Filed: Mar. 23, 2006

(51) Int. Cl.
*A61B 5/1455* (2006.01)
(52) U.S. Cl. ........................................ 600/339; 600/310
(58) Field of Classification Search ........... 600/309–344
See application file for complete search history.

(56) References Cited

U.S. PATENT DOCUMENTS

| | | | |
|---|---|---|---|
| 5,076,271 A | 12/1991 | Lekholm et al. | 128/419 PG |
| 5,328,460 A | 7/1994 | Lord et al. | 604/67 |
| 5,476,483 A | 12/1995 | Bornzin et al. | 607/17 |
| 5,676,141 A | 10/1997 | Hollub | 128/633 |
| 5,891,176 A | 4/1999 | Bornzin | 607/18 |
| 6,044,297 A | 3/2000 | Sheldon et al. | 607/17 |
| 6,122,536 A | 9/2000 | Sun et al. | 600/341 |
| 6,449,509 B1 | 9/2002 | Park et al. | 607/20 |
| 6,589,188 B1 | 7/2003 | Street et al. | 600/538 |
| 6,595,927 B2 | 7/2003 | Pitts-Crick et al. | 600/529 |
| 6,622,045 B2 | 9/2003 | Snell et al. | 607/30 |
| 6,645,153 B2 | 11/2003 | Kroll et al. | 600/481 |
| 6,942,622 B1 | 9/2005 | Turcott | 600/508 |
| 6,944,488 B2 | 9/2005 | Roberts | 600/339 |
| 2003/0109776 A1 | 6/2003 | Jacques | 600/331 |
| 2004/0102712 A1 | 5/2004 | Belalcazar et al. | 600/547 |
| 2004/0134496 A1* | 7/2004 | Cho et al. | 128/204.23 |
| 2004/0220460 A1 | 11/2004 | Roberts | 600/333 |
| 2005/0245833 A1 | 11/2005 | Kline | 600/508 |
| 2007/0021678 A1* | 1/2007 | Beck et al. | 600/510 |

FOREIGN PATENT DOCUMENTS

WO   WO 2004/098403 A1   11/2004

* cited by examiner

*Primary Examiner* — Eric Winakur
*Assistant Examiner* — Marjan Fardanesh

(57) ABSTRACT

Techniques are provided for the self-calibration of an implantable blood oxygen saturation sensor. In one example, the pacemaker tracks respiration rate, patient activity level and the degree of pulmonary edema with the patient. The pacemaker identifies periods of time when three conditions are met: the respiration rate is normal, activity is minimal and the degree of pulmonary edema is also minimal. The pacemaker then calibrates the oxygen saturation sensor based on sensor output values detected only when all three conditions are met. By calibrating the sensor only during periods of time when all three conditions are all met, the calibration logic can thereby assume that actual saturation levels within the patient are at a maximum and that any deviation from that maximum is due to changes in blood cell fixation, tissue overgrowth, or other factors unrelated to actual oxygen saturation levels.

15 Claims, 6 Drawing Sheets

SYSTEM AND METHOD FOR CALIBRATING A BLOOD OXYGEN SATURATION SENSOR FOR USE WITH AN IMPLANTABLE MEDICAL DEVICE

FIELD OF THE INVENTION

The invention generally relates to implantable medical devices, such as pacemakers or implantable cardioverter/defibrillators (ICDs), and in particular to techniques for calibrating implantable blood oxygen saturation sensors used in connection with such devices.

BACKGROUND OF THE INVENTION

Blood oxygen saturation ($SO_2$) is a measure of the amount of oxygen dissolved or carried in the blood. More specifically, blood $SO_2$ represents the percentage of hemoglobin binding sites in the bloodstream occupied by oxygen. State-of-the-art pacemakers and ICDs are typically equipped with one or more sensors for detecting blood $SO_2$, as an accurate measure of blood $SO_2$ is very useful for a variety of diagnostic purposes. For example, blood $SO_2$ is useful for tracking cardiac output within the patient, i.e. the amount of blood pumped by the heart per minute. See, e.g., U.S. Patent Application 2005/0245833 of Kline entitled "Non-Invasive Device and Method for Measuring the Cardiac Output of a Patient." Blood $SO_2$ is also used to evaluate autonomic tone. See, e.g., U.S. Pat. No. 6,942,622 to Turcott, "Method for Monitoring Autonomic Tone." Blood $SO_2$ is useful for controlling pacing therapy so as to achieve hemodynamically optimal therapy. See, e.g., U.S. Pat. No. 5,891,176 to Bornzin, entitled "System and Method for Providing Hemodynamically Optimal Pacing." Blood $SO_2$ may also be employed as an indictor of physical activity within a patient. See, e.g., U.S. Pat. No. 5,076,271 to Lekholm, et al., entitled "Rate-Responsive Pacing Method and System Employing Minimum Blood Oxygen Saturation as a Control Parameter and as a Physical Activity Indicator."

Blood $SO_2$ is also advantageously employed in connection with detecting various respiratory conditions such as apnea or periodic breathing. See, e.g., U.S. patent application Ser. No. 10/795,009, of Koh, entitled "System and Method for Distinguishing among Obstructive Sleep Apnea, Central Sleep Apnea and Normal Sleep Using an Implantable Medical System," filed Mar. 4, 2004. Blood $SO_2$ may also be used as one factor in evaluating heart failure and associated mortality. See, e.g., U.S. Pat. No. 6,645,153, to Kroll et al., entitled "System and Method for Evaluating Risk of Mortality Due To Congestive Heart Failure Using Physiologic Sensors" and U.S. Pat. No. 6,589,188 of Street, et al., "Method for Monitoring Heart Failure via Respiratory Patterns". Depending upon the particular application, either arterial $SO_2$ (i.e. $SaO_2$), or venous $SO_2$ (i.e. $SvO_2$), or both, may be detected and exploited.

Unfortunately, blood $SO_2$ is a difficult parameter for a pacemaker or other implantable medical device to accurately and reliably detect. To detect blood $SO_2$, pacemakers typically employ an implanted optical sensor that includes a light emitting diode (LED), which transmits light into blood passing the sensor, and a phototransistor that senses the light after it has passed through the blood. Blood $SO_2$ is then derived from a comparison of the intensity and frequency of the emitted light and the received light. In particular, pulse oximetry techniques are often employed by the pacemaker to determine the blood $SO_2$ level from the light signals. See, e.g., U.S. Pat. No. 5,676,141 to Hollub, entitled "Electronic Processor for Pulse Oximeters." Depending upon the implementation, an optical measurement window of the phototransistor of the sensor is either positioned within the blood stream (such as within one of the chambers of the heart) or is positioned subcutaneously near a blood vessel. If the measurement window is positioned in the blood stream, blood cells tend to fixate on the optical measurement window thus interfering with the sensor. If the measurement window is instead is mounted subcutaneously, then skin and/or muscle cells can grow over the window, likewise interfering with the sensor. Moreover, the intensity of the LED tends to decrease over its life time.

Hence, implantable blood $SO_2$ sensors should be periodically calibrated to compensate for these and other factors. Calibration may be performed in conjunction with an external detector. The blood $SO_2$ level within the patient is simultaneously detected using both the implanted sensor and the external detector. If the two values differ, a calibration factor is calculated to adjust the internally detected saturation value to match the externally detected value. The calibration is then repeated periodically, perhaps every several months or so, in an attempt compensate for blood cell fixation, tissue overgrowth, and other factors. Unfortunately, a significant amount of blood cell fixation or tissue overgrowth can occur in the interim, greatly affecting the output values of the sensor such that the pacemaker no longer receives correct saturation values, which may in turn lead to pacing that is counter-productive and perhaps even dangerous for the patient.

As can be appreciated, it would be far more desirable to provide a self-calibration technique that can be performed by the implanted system itself without need for a simultaneously-detected external oxygen saturation measurement. Such a calibration technique would allow the pacemaker to frequently adjust the calibration factors so as to promptly compensate for changes in blood cell fixation, tissue overgrowth, etc. One possible self calibration technique involves comparing the latest output signals from the sensor with previously detected and stored baseline signals. Any difference between the new output signals and the baseline signals is then attributed to changes in blood cell fixation, tissue overgrowth, etc., and appropriate calibration factors are calculated. A fundamental problem with the proposed technique is that it assumes that the actual blood $SO_2$ level within the patient is the same for the newly sensed signals and for the baseline signals. If not, then any difference between the newly sensed signals and the baseline signals may be due to a difference in oxygen saturation instead of a difference in blood cell fixation or tissue overgrowth. In other words, the proposed technique, without further inventive modifications, cannot distinguish between variations in the sensed signals arising due to changes in oxygen saturation and variations due to other factors and hence is unable to properly calibrate the sensor.

Accordingly, it would be highly desirable to provide an effective self calibration technique for use with an implantable blood $SO_2$ sensor and it is to this end that the invention is primarily directed.

SUMMARY

In accordance with certain embodiments, techniques are provided for calibrating an implantable blood $SO_2$ sensor for use with an implantable medical system. In one example, values representative of one or more of respiration rate, patient activity and degree of pulmonary edema are detected within the patient. A period of time is identified wherein the detected values are each within predetermined acceptable ranges. A calibration factor is then determined based on blood $SO_2$ sensor signals detected during the period of time. The blood $SO_2$ sensor is then calibrated using the calibration factor.

In one particular example, the calibration factor is calculated by: measuring a new $SO_2$ value using the blood $SO_2$ sensor; retrieving a stored $SO_2$ value obtained during a previous period of time when the detected values were also each within predetermined acceptable ranges; and then calculating a calibration factor as the ratio of the newly measured $SO_2$ value and the stored $SO_2$ value. The $SO_2$ sensor is then calibrated using the new calibration factor by multiplying all new values sensed using the oxygen saturation sensor by the calibration factor. Preferably, respiration rate, patient activity and degree of pulmonary edema are each detected. The identified period of time corresponds to a time interval when respiration rate is normal, activity is minimal and pulmonary edema is also minimal, i.e. a period of time is identified when all three conditions are met.

In this regard, $SO_2$ values are substantially at their maximum levels within a patient (typically about 97% for $SaO_2$) when the three conditions are met. Although the particular maximum level of saturation may differ from patient to patient, the maximum for a given patient typically does not change significantly over time (or, if it changes, it changes only slowly compared to other factors). Hence, by calibrating the oxygen saturation sensor using only blood $SO_2$ sensor signals detected during periods of time when all three conditions are met, the calibration logic can thereby assume that any changes in the sensor signals are not due to changes in actual blood $SO_2$. In other words, blood $SO_2$ is assumed to be at a maximum baseline level during those periods of time. Any deviations from the baseline are assumed to be due to changes in blood cell fixation, tissue overgrowth, etc., rather than changes in actual oxygen saturation levels.

Hence, techniques are provided for automatically calibrating an implantable blood $SO_2$ sensor while taking respiration rate, patient activity and degree of pulmonary edema into account. Any changes in the calculated calibration factor over time are preferably tracked by the implanted device and any trends are detected. This information may be used by a physician for diagnostic purposes or by the device itself to automatically adjust the calibration factor between recalibration times. Depending upon the implementation, recalibration may be performed daily. If recalibration cannot be performed over an extended period of time—due to the lack of any time periods when all three of the aforementioned conditions are met—then suitable warning signals are preferably generated indicating that the sensor may need to be recalibrated using an external system. As this situation may arise due to progression of pulmonary edema within the patient, suitable warning signals are preferably generated so as to notify a physician or other medical professional. The invention is preferably applied to arterial blood oxygen sensors ($SaO_2$) but may also be advantageously applied to venous blood oxygen sensors ($SvO_2$).

BRIEF DESCRIPTION OF THE DRAWINGS

The above and further features, advantages and benefits of the present invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
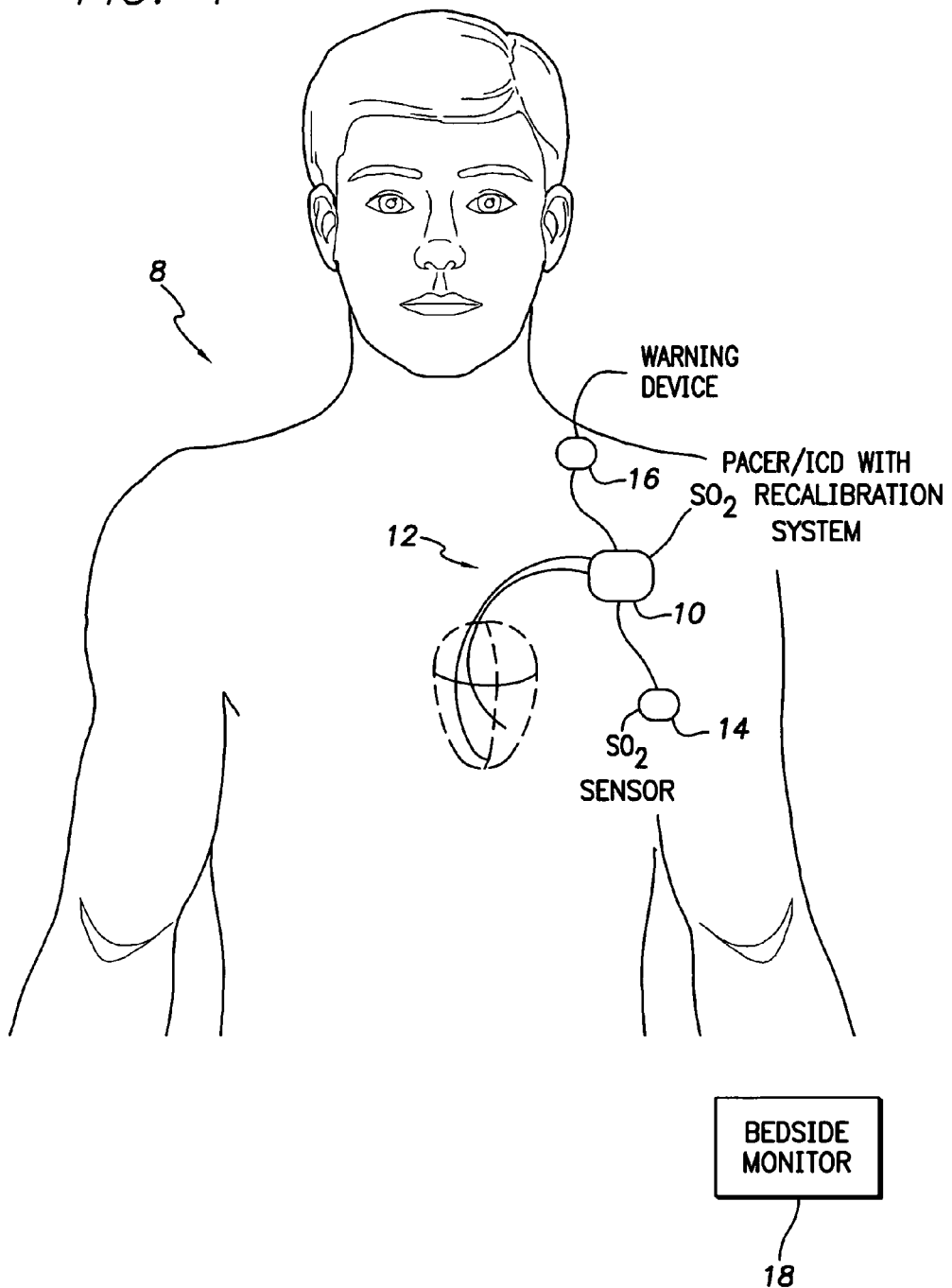
FIG. 1 illustrates pertinent components of an implantable medical system having a pacemaker or ICD capable of automatically calibrating an implanted blood $SO_2$ sensor.
Figure 5:
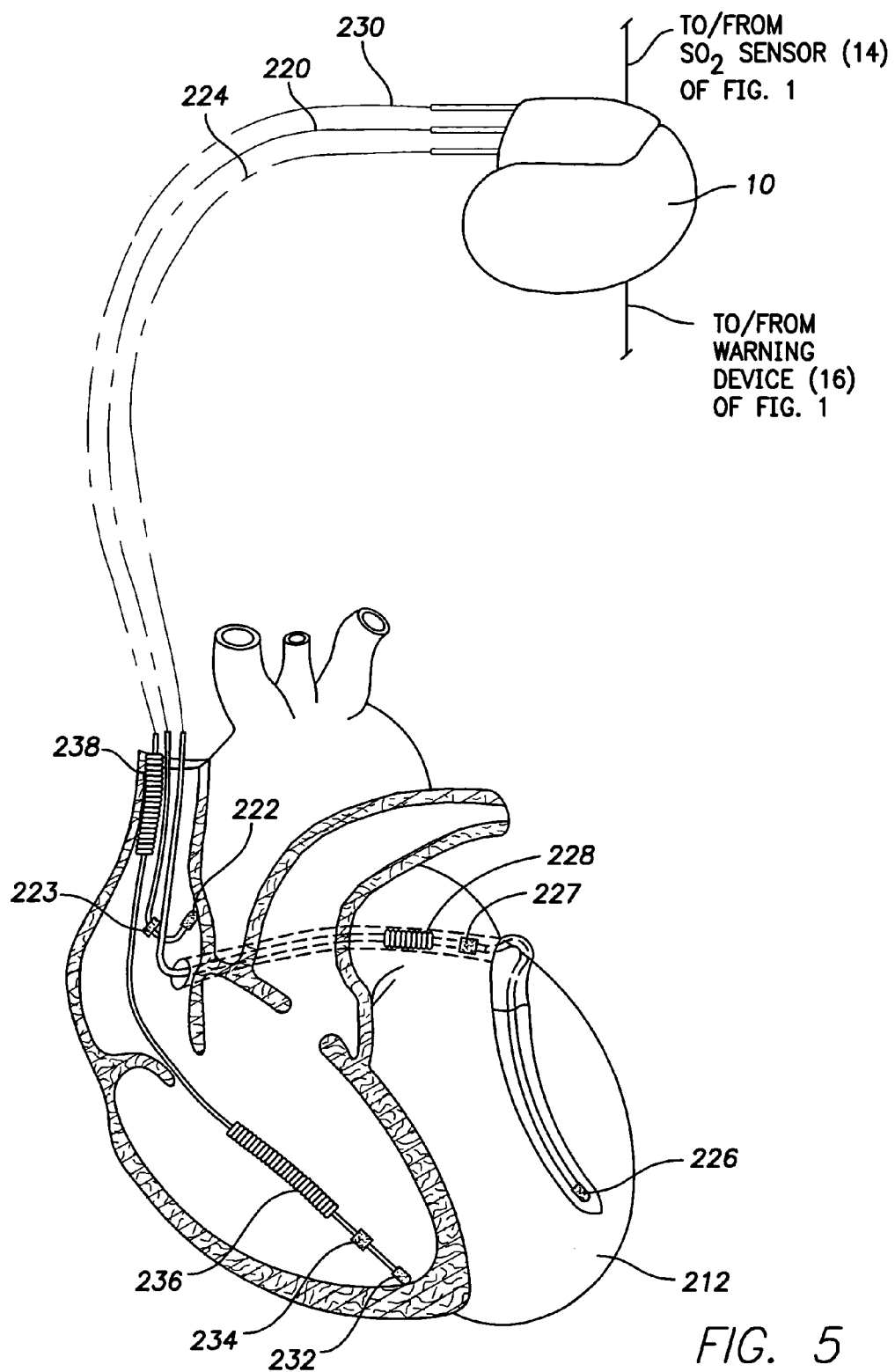
FIG. 5 is a simplified, partly cutaway view, illustrating the pacer/ICD of FIG. 1 along with at set of leads implanted into the heart of a patient.

FIG. 1 illustrates an implantable medical system 8 having a pacer/ICD 10 and set of pacing/sensing leads 12 implanted within the heart. (Within FIG. 1, only two leads are shown. A more complete set of leads is illustrated in FIG. 5 and described below.) The system also includes an implanted arterial blood $SO_2$ sensor 14 for sensing signals representative of $SaO_2$ levels via otherwise conventional techniques such as pulse oximetry. In the example of FIG. 1, the sensor is shown as being implanted separately from the pacer/ICD and its leads. In many implementations, however, the sensor is mounted to one of the pacing/sensing leads for positioning within a chamber of the heart. Further, although an arterial sensor is shown, principles of the invention are applicable to venous sensors as well.

Based on signals received from the sensor, the pacer/ICD determines the current $SaO_2$ level of the patient. The sensor may operate substantially continuously so that the pacer/ICD can track oxygen saturation levels throughout the day. Depending upon the particular implementation, the pacer/ICD may use the oxygen saturation values to diagnose medical conditions and to control pacing or other therapy. As already explained, blood $SO_2$ sensors should be calibrated frequently to compensate for blood cell fixation, tissue overgrowth or other factors. Accordingly, pacer/ICD includes a blood $SO_2$ calibration system that identifies periods of time when the sensor can be reliably calibrated and then automatically calibrates the sensor during those periods of time. More specifically, the pacer/ICD uses additional sensors (not shown in FIG. 1) to identify periods of time when the respiration rate of the patient is normal, patient activity is minimal and any pulmonary edema within the patient is also minimal. Pulmonary edema is a swelling and/or fluid accumulation in the lungs often caused by heart failure (i.e. the edema represents one of the "congestives" of congestive heart failure.) Briefly, the poor cardiac function resulting from heart failure can cause blood to back up in the lungs, thereby increasing blood pressure in the lungs. The increased pressure pushes fluid—but not blood cells—out of the blood vessels and into lung tissue and air sacs. By calibrating the oxygen sensor at times when the three conditions are all met, the pacer/ICD can thereby properly distinguish between variations in sensor output values arising due to blood cell fixation or tissue overgrowth and variations arising due to changes in oxygen saturation within the patient caused by variations in activity, respiration rate or the degree of pulmonary edema.

The pacer/ICD also tracks changes in the calibration factor to identify any trends and stores appropriate diagnostic data. Circumstances may arise wherein the pacer/ICD is unable to calibrate the oxygen saturation sensor over an extended period of time, such as a month or more. This may occur, e.g., if pulmonary edema progresses within the patient to the point where there are no longer any periods with minimal edema. Hence, the pacer/ICD generates warning signals indicating that calibration has not been performed recently and that the blood $SO_2$ values may no longer be as accurate as desired. As this situation may arise due to progression of pulmonary edema within the patient, the warning signals may further identify pulmonary edema as the possible source of the problem. The warning signals may be applied directly to the patient via an implanted warning device 16, which may be, for example, a vibrating device or a "tickle" voltage device that, in either case, provides perceptible stimulation to the patient to alert the patient to have the implantable system checked by a physician or other medical professional. "Tickle" warning device are discussed in U.S. Pat. No. 5,328, 460 to Lord, et al., entitled "Implantable Medication Infusion Pump Including Self-Contained Acoustic Fault Detection Apparatus." Warning signals may additional or alternatively be transmitted to a bedside monitor 18, which generates audible or visual warnings. The bedside monitor may be networked with other external systems so as to automatically forward the warnings to a physician or other medical professional. A system incorporating bedside monitoring units connected to a centralized external programmer system is described in U.S. Pat. No. 6,622,045 to Snell et al., "System and Method for Remote Programming of Implantable Cardiac Stimulation Devices."

Thus, FIG. 1 provides an overview of an implantable system for automatically calibrating an implanted blood $SO_2$ sensor. It should be appreciated that systems provided in accordance with invention need not include all of the components shown in FIG. 1. In many cases, for example, the system will include only the pacer/ICD and its leads and the blood $SO_2$ sensor, but no implanted warning device. Still other implementations may employ additional components, such as separate venous and arterial blood $SO_2$ sensors. These are just a few exemplary embodiments. No attempt is made herein to describe all possible combinations of components that may be provided in accordance with the general principles of the invention. Although, internal signal transmission lines for interconnecting the various implanted components are shown, wireless signal transmission may alternatively be employed. Note also that the particular sizes and locations of the implanted components are merely exemplary and actual implant locations may differ.

Overview of Calibration Technique

Figure 2:
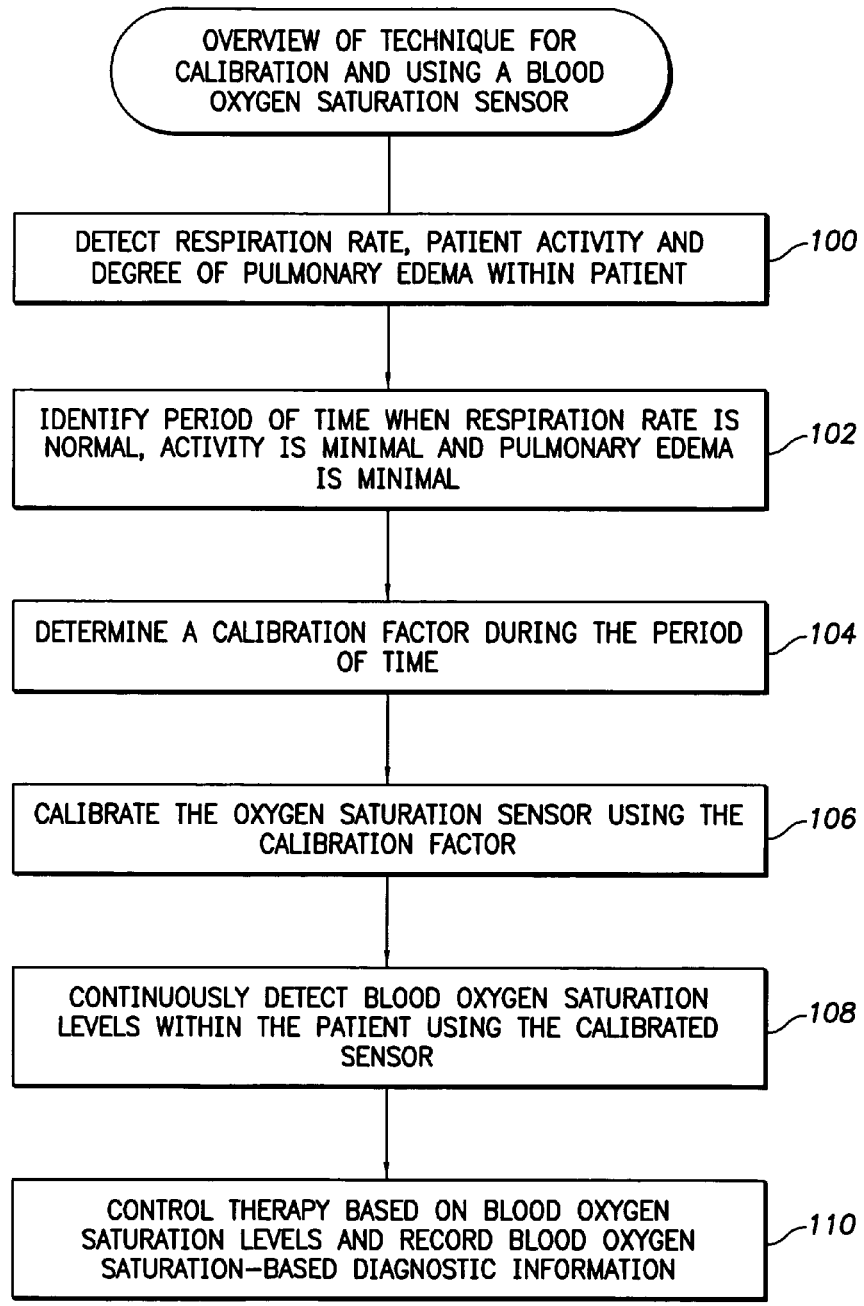
FIG. 2 is a flow chart providing an overview of the calibration method performed by the system of FIG. 1.

FIG. 2 provides an overview of the calibration techniques of the invention. Initially, at step 100, the pacer/ICD detects respiration rate, patient activity and degree of pulmonary edema within patient. Respiration rate may be detected based on an analysis of trans-thoracic impedance sensed between an electrode implanted within the heart and an electrode connected to the housing of the pacer/ICD, using otherwise conventional techniques. See, for example, U.S. Pat. No. 6,449, 509 to Park, et al., entitled "Implantable Stimulation Device Having Synchronous Sampling for a Respiration Sensor." However, alternative techniques may instead be employed for detecting respiration rate, depending upon the implementation. See, for example, U.S. patent application Ser. No. 11/100,189 of Koh, entitled "System and Method for Detection of Respiration Patterns via Integration of Intracardiac Electrogram Signals."

The degree of pulmonary edema may also be detected based on an analysis of trans-thoracic impedance. In one example, the trans-thoracic impedance signals are averaged over several respiration cycles so as to eliminate variations due to respiration. The average trans-thoracic impedance is thereby primarily representative of the degree of pulmonary edema, as the congestives associated with edema significantly affect the electrical impedance through the thorax. See, for example, U.S. patent application Ser. No. 11/138,229 of Koh, entitled "System and Method for Impedance-Based Detection of Pulmonary Edema and Reduced Respiration Using an Implantable Medical System." See, also, U.S. Pat. No. 6,595,927 to Pitts-Crick et al., entitled "Method and System for Diagnosing and Administering Therapy of Pulmonary Congestion" and U.S. Patent Application 2004/0102712 of Belalcazar et al., entitled "Impedance Monitoring for Detecting Pulmonary Edema and Thoracic Congestion." However, alternative edema detection techniques may instead be employed, depending upon the implementation, that does not necessarily rely on trans-thoracic impedance. See, for example, U.S. patent application Ser. No. 11/100,008, of Kil et al., entitled "System and Method for Detecting Heart Failure and Pulmonary Edema Based on Ventricular End-Diastolic Pressure Using an Implantable Medical Device."

Patient activity may be detected using an accelerometer or other physical activity sensor mounted within the pacer/ICD itself or positioned elsewhere within the patient. Depending upon the implementation, the physical activity sensor may be employed in conjunction with an "activity variance" sensor, which monitors the activity sensor diurnally to detect the low variance in the measurement corresponding to a rest state. For a complete description of an activity variance sensor, see U.S. Pat. No. 5,476,483 to Bornzin et al., entitled "System and Method for Modulating the Base Rate during Sleep for a Rate-Responsive Cardiac Pacemaker."

Although, respiration rate, patient activity and degree of pulmonary edema are preferably each detected, in some implementations, only a subset of these parameters is detected, such as only respiration rate and patient activity. This may be appropriate, for example, within patient known to have no pulmonary edema. In other implementations, additional parameters are detected and exploited. For example, it may be appropriate to calibrate the blood oxygen sensor only during a period of time wherein—in addition to normal respiration rate, minimal activity and minimal edema—the patient is also known to be lying down. This is because there will generally be less "noise" when the patient is lying down, i.e. the detected parameters will be more immune to signal artifacts caused by patient artifacts. Hence, by only calibrating while the patient is known to by lying down, a more precise calibration may be achieved. Techniques for detecting patient posture or changes in posture are set forth in U.S. patent application Ser. No. 10/329,233, of Koh et al., entitled "System and Method for Determining Patient Posture Based On 3-D Trajectory Using an Implantable Medical Device". Other techniques are set forth in U.S. Pat. No. 6,044,297 to Sheldon, et al. "Posture and Device Orientation and Calibration for Implantable Medical Devices."

At step 102, the pacer/ICD identifies a period of time when each of the detected values are within predetermined acceptable ranges, e.g. the patient respiration rate is normal, patient activity level is minimal and the degree of pulmonary edema is minimal. This may be achieved using suitable threshold values discussed below in connection with FIG. 3 or by using any other suitable technique. As summarized above, $SO_2$ values are substantially at their maximum levels within a patient (typically about 97% for $SaO_2$) when the three conditions are met. Insofar as activity is concerned, an increase in activity generally reduces blood $SO_2$ primarily due to the increase in carbon dioxide and excess water within the blood that results from muscle usage during activity. Hence, maximum blood $SO_2$ occurs when activity is minimal. Pulmonary edema tends to decrease the alveolar gas exchange area leading to hypercapina/hypoxia, thus reducing blood $SO_2$. Hence, maximum blood $SO_2$ occurs with minimal pulmonary edema. Insofar as respiration is concerned, abnormally low respiration will prevent sufficient oxygen from reaching the blood stream thus reducing blood $SO_2$. Within healthy patient, blood $SO_2$ will likely be at its maximum for high respiration rates. However, blood $SO_2$ will not be at its maximum in patients subject to respiratory alkalosis during high respiration rates. Hence, the primary reason for excluding high respiration rates is to avoid the possibility that respiratory alkalosis might affect the calibration.

At step 104, the pacer/ICD determines a calibration factor (or factors) during the period of time for calibrating the blood $SO_2$ sensor. As explained above in the Summary, blood $SO_2$ values are substantially at their maximum levels within a patient (and typically about 97% for $SaO_2$) when respiration rate is normal, patient activity is minimal and pulmonary edema is also minimal. The particular maximum level of saturation may differ from patient to patient. However, the maximum for a given patient either does not change significantly over time or changes relatively slowly compared to other factors, such as blood cell fixation. Hence, by calibrating the oxygen saturation sensor using only blood $SO_2$ sensor signals detected during periods of time when patient respiration rate is normal, patient activity is minimal and pulmonary edema is minimal, the calibration logic can thereby assume that any changes in the sensor signals are not due to changes in actual blood $SO_2$.

The particular calibration factor or factors calculated at step 106 depend upon the particular sensor being used. Typically, blood $SO_2$ sensors output a single voltage value representative of the blood saturation value. With such sensors, the calibration factor is simply a numerical value for multiplying against the voltage values to compensate for any changes in the sensor output over time not due to changes in actual oxygen saturation. A more detail example is discussed below in connection with FIG. 3. Also, although not explicitly shown in FIG. 2, the implantable system is preferably recalibrated occasionally (e.g. once per year) using externally derived oxygen saturation measurements, since the maximum blood saturation level possible within the patient may very slowly over time.

At step 108, the pacer/ICD detects blood $SO_2$ levels using the calibrated sensor and, at step 110, controls therapy based, in part, on blood $SO_2$ levels, in accordance with otherwise conventional techniques. For example, the techniques of U.S. Pat. No. 5,891,176 to Bornzin, (cited above) may be employed for controlling pacing therapy so as to achieve hemodynamically optimal therapy. In addition, at step 110, the pacer/ICD records any appropriate diagnostic information that relates to, or exploits, blood $SO_2$ levels. For example, autonomic tone may be evaluated using the techniques of U.S. Pat. No. 6,942,622 to Turcott (cited above). Heart failure and associated mortality may be evaluated based, in part, on oxygen saturation levels using techniques described in U.S. Pat. No. 6,645,153 to Kroll et al. and U.S. Pat. No. 6,589,188 to Street, et al. (both cited above).

Figure 3:
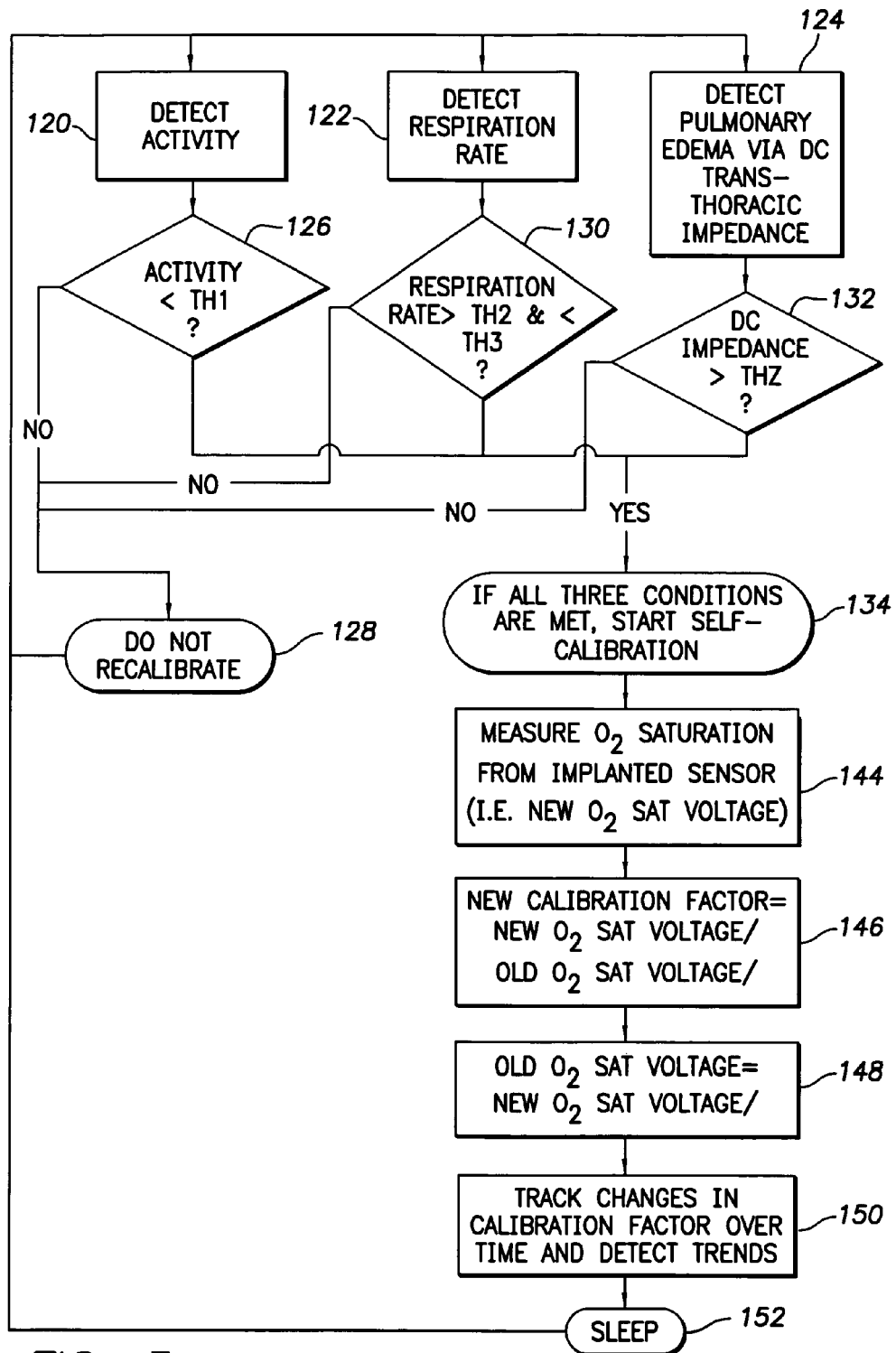
FIG. 3 is a flow chart illustrating an exemplary calibration procedure performed in accordance with the general technique of FIG. 2.
Figure 4:
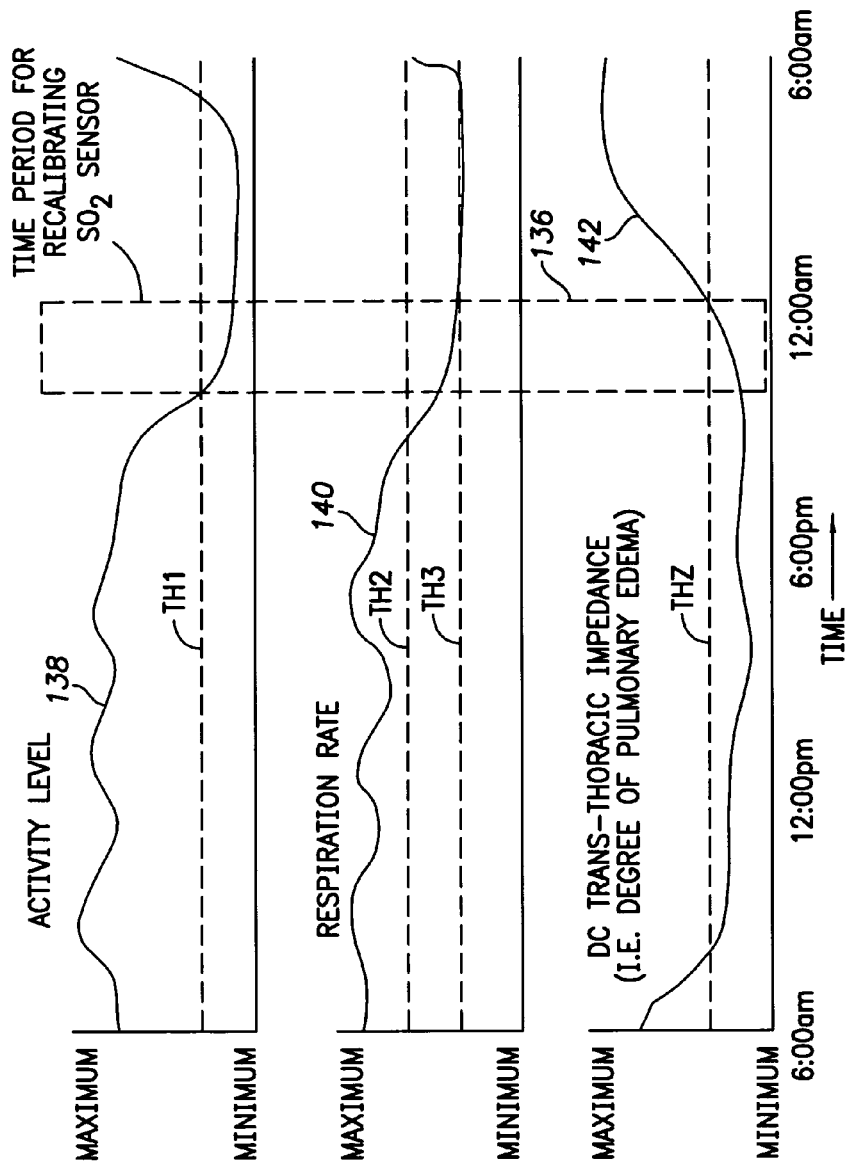
FIG. 4 is a stylized graph illustrating exemplary variations in respiration rate, activity level and degree of edema tracked by the calibration procedure of FIG. 3.

Turning now to FIGS. 3 and 4, an exemplary embodiment employing various predetermined threshold values will now be described. While the pacer/ICD performs other conventional functions, it also continuously tracks patient activity, step 120, respiration rate, step 122, and degree of pulmonary edema, step 124. Activity is compared, at step 126, against a first threshold (TH1) representative of a maximum acceptable level of activity for the purposes of blood $SO_2$ sensor calibration. Depending upon the implementation, TH1 may be preprogrammed during device design to a default value or may be set by the pacer/ICD based on actual activity variations of the patient. For example, the pacer/ICD may track the range of activity levels of the patient and set TH1 to represent an activity level that corresponds to, e.g., only 5% of the patient's typical daily maximum activity level. In any case, if the activity level exceeds TH1, then no calibration is performed, step 128, since the actual blood $SO_2$ level within the patient may not be at its maximum due to too much patient movement. Processing instead returns to steps 120, 122, and 124 to track additional values. In some implementations, the implanted device estimates metabolic oxygen demand based on patient activity and then compares metabolic oxygen demand against a suitable threshold value.

Meanwhile, respiration rate is compared, at step 130, against upper and lower threshold values (TH2 and TH3) representative, respectively, of a minimum and maximum acceptable respiration rates for the purposes of blood $SO_2$ sensor calibration. If the respiration rate falls outside the two thresholds, then no calibration is performed, step 128, since the actual blood $SO_2$ level within the patient may not be at its maximum due to abnormal respiration rates. After step 130, processing returns to steps 120, 122, and 124 to track additional values. Depending upon the implementation, TH2 and TH3 may be preprogrammed during device design to default values or may be set by the pacer/ICD based on actual respiration rate variations of the patient. For example, the pacer/ICD may track the range of respiration rates of the patient and set the thresholds to encompass respiration rates corresponding to, e.g., 80% of the patient's typical respiration rates, thereby excluding extremely low and extremely high respiration rates, which might reduce oxygen saturation.

Simultaneously, the direct current (DC) trans-thoracic impedance is compared, at step 132, against a threshold value (THZ) representative of a maximum acceptable degree of pulmonary edema for the purposes of blood $SO_2$ sensor calibration. Preferably, impedance is measured during the peak of expiration when the signal is most strongly correlated with the degree of lung fluid. Impedance values may also be averaged. In any case, if the measured thoracic impedance is below the threshold (indicative of too much edema), then no calibration is performed, step 128 since the actual blood $SO_2$ level within the patient may not be at its maximum due to the presence of elevated levels of pulmonary edema. As before, processing instead returns to steps 120, 122, and 124 to track additional values. Depending upon the implementation, THZ may be preprogrammed during device design to a default value or may be set by the physician based, e.g., on whether the patient is already know to have pulmonary edema.

However, if each of the three conditions is met at steps 126, 130 and 132 (indicating that the blood $SO_2$ level of the patient is at its maximum), then a self-calibration procedure begins at step 134. A period of time where each of the three conditions is met is shown in FIG. 4 by way of interval 136. As can be seen, during that interval, and only during that interval, patient activity 138 is below threshold TH1, patient respiration rate 140 is between thresholds TH2 and TH3, and the DC trans-thoracic impedance 142 is also below THZ indicating minimal pulmonary edema. Note that the graphs of FIG. 4 are stylized representations of hypothetical data provided to illustrate features of the invention and should not be construed as representing actual clinical data. The scales of the vertical axes are arbitrary. In the example of FIG. 4, the three parameters (activity, respiration rate and DC trans-thoracic impedance) are shown varying over the course of one day, with diminished activity levels and respiration rates occurring at night while the patient is asleep. For this particular patient, pulmonary edema is less severe during the day, since the patient is more active, and becomes more severe at night.

Returning to FIG. 3, at step 144, the pacer/ICD measures oxygen saturation using the implanted sensor, i.e. new sensor voltage values are obtained. Multiple sensor values may be averaged to smooth out very short term variations due to, for example, respiration and cardiac beating. At step 146, the pace/ICD then calculates a new calibration factor as the new (averaged) sensor voltage divided by the previous (averaged) sensor voltage, i.e. the sensor voltage detected the last time the sensor was calibrated, which is retrieved from memory. At step 148, the pacer/ICD then updates the memory to replace the old sensor voltage with the new sensor voltage for use during a subsequent recalibration procedure. At step 150, the pacer/ICD also evaluates any changes in the calibration factor over time and identifies any trends. In this regard, the pacer/ICD may store each new calibration factor and the date/time it was obtained for analysis. A significant change in the calibration factor may be detected using suitable threshold values and appropriate diagnostic data may be stored for subsequent physician review. A sharp change in the calibration factor may be indicative, for example, of a possible malfunction in the sensor. Thereafter, the calibration procedure "sleeps" for some predetermined period of time before processing returns to steps 120, 122 and 124 to track new values of the parameters in expectation of a new calibration procedure. The calibration procedure sleeps so as to prevent the pacer/ICD from repeatedly recalibrating the sensor during a single interval wherein the three conditions or all met or during a series of closely spaced intervals. In one example, the pacer/ICD sleeps at least for twenty-four hours so that calibration is performed, at most, once per day.

Although not shown in FIG. 4, if the calibration procedure is not performed even once over some extended period of time (such as one month)—due to a lack of any intervals wherein the three conditions are all met—then the pacer/ICD generates the above-described warning signals indicative of a possible progression of pulmonary edema within the patient. In this regard, it is generally expected that there are many intervals during the day when respiration rate is normal and activity is minimal. Hence, failure to calibrate is likely due to the fact that pulmonary edema has progressed to the point where DC trans-thoracic impedance is consistently above the THZ threshold, preventing calibration.

What have been described are various techniques for calibrating a blood $SO_2$ sensor. For the sake of completeness, a detailed description of an exemplary pacer/ICD for performing these functions will now be provided. However, principles of invention may be implemented within other pacer/ICD implementations.

Exemplary Pacemaker/ICD

Figure 6:
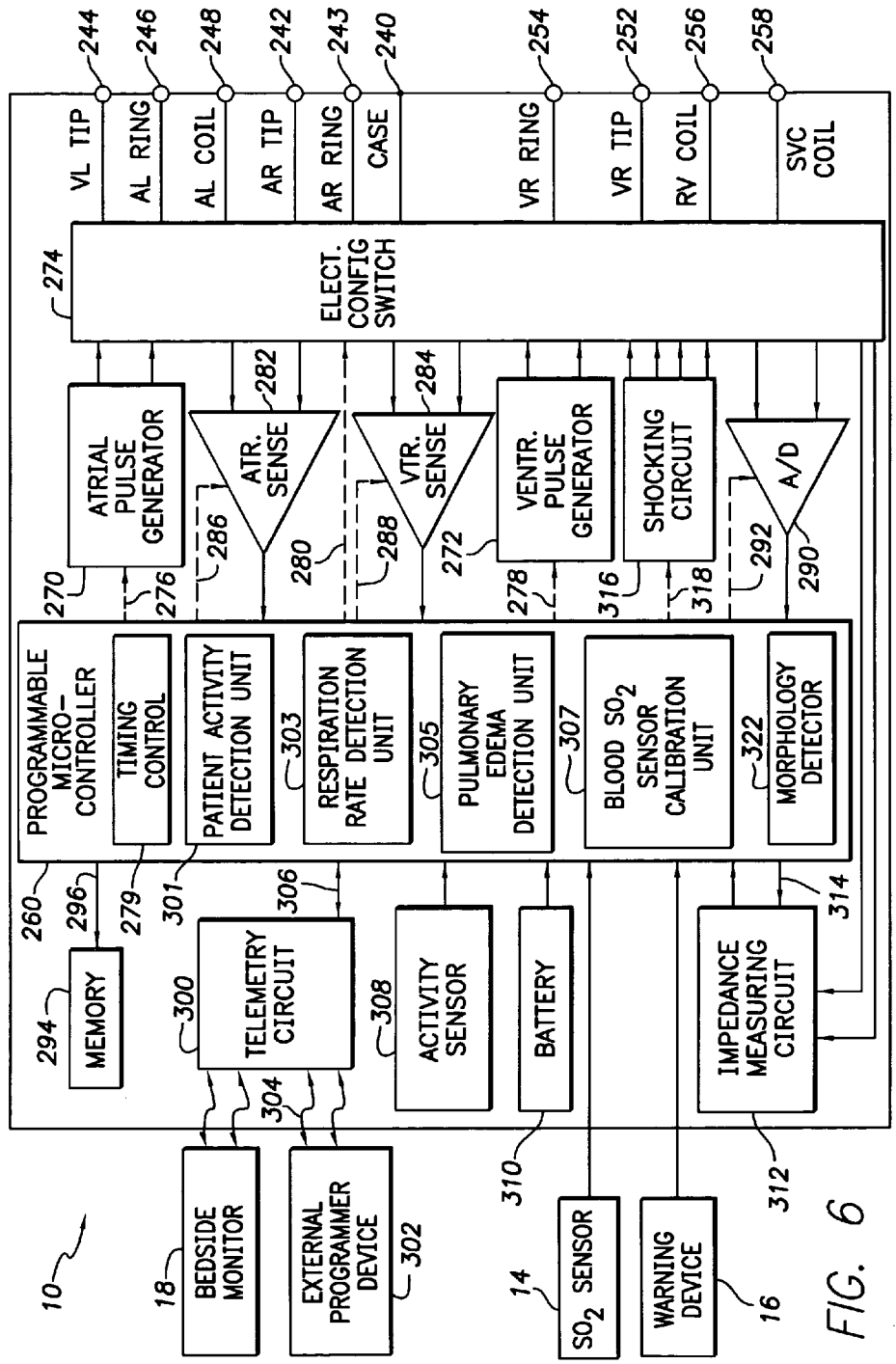
FIG. 6 is a functional block diagram of the pacer/ICD of FIG. 5, illustrating basic circuit elements that provide cardioversion, defibrillation and/or pacing stimulation in four chambers of the heart and particularly illustrating components for calibrating the blood $SO_2$ sensor.

With reference to FIGS. 5 and 6, a detailed description of the pacer/ICD of FIG. 1 will now be provided. FIG. 5 provides a simplified block diagram of the pacer/ICD, which is a dual-chamber stimulation device capable of treating both fast and slow arrhythmias with stimulation therapy, including cardioversion, defibrillation, and pacing stimulation, as well as capable of detecting apnea and controlling delivering of therapy in response thereto. To provide atrial chamber pacing stimulation and sensing, pacer/ICD 10 is shown in electrical communication with a heart 212 by way of a left atrial lead 220 having an atrial tip electrode 222 and an atrial ring electrode 223 implanted in the atrial appendage. Pacer/ICD 10 is also in electrical communication with the heart by way of a right ventricular lead 230 having, in this embodiment, a ventricular tip electrode 232, a right ventricular ring electrode 234, a right ventricular (RV) coil electrode 236, and a superior vena cava (SVC) coil electrode 238. Typically, the right ventricular lead 230 is transvenously inserted into the heart so as to place the RV coil electrode 236 in the right ventricular apex, and the SVC coil electrode 238 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 224 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 224 is designed to receive atrial and ventricular cardiac signals and to deliver left ventricular pacing therapy using at least a left ventricular tip electrode 226, left atrial pacing therapy using at least a left atrial ring electrode 227, and shocking therapy using at least a left atrial coil electrode 228. With this configuration, biventricular pacing can be performed. Although only three leads are shown in FIG. 5, it should also be understood that additional stimulation leads (with one or more pacing, sensing and/or shocking electrodes) may be used in order to efficiently and effectively provide pacing stimulation to the left side of the heart or atrial cardioversion and/or defibrillation.

A simplified block diagram of internal components of pacer/ICD 10 is shown in FIG. 6. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 240 for pacer/ICD 10, shown schematically in FIG. 6, is often referred to as the "can", "case" or "case electrode" and may be programmably selected to act as the return electrode for all "unipolar" modes. The housing 240 may further be used as a return electrode alone or in combination with one or more of the coil electrodes, 228, 236 and 238, for shocking purposes. The housing 240 further includes a connector (not shown) having a plurality of terminals, 242, 243, 244, 246, 248, 252, 254, 256 and 258 (shown schematically and, for convenience, the names of the electrodes to which they are connected are shown next to the terminals). As such, to achieve right atrial sensing and pacing, the connector includes at least a right atrial tip terminal ($A_R$ TIP) 242 adapted for connection to the atrial tip electrode 222 and a right atrial ring ($A_R$ RING) electrode 243 adapted for connection to right atrial ring electrode 223. To achieve left chamber sensing, pacing and shocking, the connector includes at least a left ventricular tip terminal ($V_L$ TIP) 244, a left atrial ring terminal ($A_L$ RING) 246, and a left atrial shocking terminal ($A_L$ COIL) 248, which are adapted for connection to the left ventricular ring electrode 226, the left atrial tip electrode 227, and the left atrial coil electrode 228, respectively. To support right chamber sensing, pacing and shocking, the connector further includes a right ventricular tip terminal ($V_R$ TIP) 252, a right ventricular ring terminal ($V_R$ RING) 254, a right ventricular shocking terminal ($R_V$ COIL) 256, and an SVC shocking terminal (SVC COIL) 258, which are adapted for connection to the right ventricular tip electrode 232, right ventricular ring electrode 234, the RV coil electrode 236, and the SVC coil electrode 238, respectively.

At the core of pacer/ICD 10 is a programmable microcontroller 260, which controls the various modes of stimulation therapy. As is well known in the art, the microcontroller 260 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design and operation of the microcontroller 260 are not critical to the invention. Rather, any suitable microcontroller 260 may be used that carries out the functions described herein. The use of microprocessor-based control circuits for performing timing and data analysis functions are well known in the art.

As shown in FIG. 6, an atrial pulse generator 270 and a ventricular pulse generator 272 generate pacing stimulation pulses for delivery by the right atrial lead 220, the right ventricular lead 230, and/or the coronary sinus lead 224 via an electrode configuration switch 274. It is understood that in order to provide stimulation therapy in each of the four chambers of the heart, the atrial and ventricular pulse generators, 270 and 272, may include dedicated, independent pulse generators, multiplexed pulse generators or shared pulse generators. The pulse generators, 270 and 272, are controlled by the microcontroller 260 via appropriate control signals, 276 and 278, respectively, to trigger or inhibit the stimulation pulses.

The microcontroller 260 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, combipolar, etc.) by selectively closing the appropriate combination of switches (not shown) as is known in the art. Moreover, as the explained in greater detail below, the microcontroller transmits signals to controlling the switch to connect a different set of electrodes during a far-field overdrive pacing than during near-field overdrive pacing.

Atrial sensing circuits 282 and ventricular sensing circuits 284 may also be selectively coupled to the right atrial lead 220, coronary sinus lead 224, and the right ventricular lead 230, through the switch 274 for detecting the presence of cardiac activity in each of the four chambers of the heart. Accordingly, the atrial (ATR. SENSE) and ventricular (VTR. SENSE) sensing circuits, 282 and 284, may include dedicated sense amplifiers, multiplexed amplifiers or shared amplifiers. The switch 274 determines the "sensing polarity" of the cardiac signal by selectively closing the appropriate switches, as is also known in the art. In this way, the clinician may program the sensing polarity independent of the stimulation polarity. Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 282 and 284, are connected to the microcontroller 260 which, in turn, are able to trigger or inhibit the atrial and ventricular pulse generators, 270 and 272, respectively, in a demand fashion in response to the absence or presence of cardiac activity in the appropriate chambers of the heart.

For arrhythmia detection, pacer/ICD 10 utilizes the atrial and ventricular sensing circuits, 282 and 284, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 260 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 290. The data acquisition system 290 is configured to acquire intracardiac electrogram signals, convert the raw analog data into a digital signal, and store the digital signals for later processing and/or telemetric transmission to an external device $3_{02}$. The data acquisition system 290 is coupled to the right atrial lead 220, the coronary sinus lead 224, and the right ventricular lead 230 through the switch 274 to sample cardiac signals across any pair of desired electrodes. The microcontroller 260 is further coupled to a memory 294 by a suitable data/address bus 296, wherein the programmable operating parameters used by the microcontroller 260 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 294 through a telemetry circuit 300 in telemetric communication with the external device 302, such as a programmer, transtelephonic transceiver or a diagnostic system analyzer. The telemetry circuit 300 is activated by the microcontroller by a control signal 306. The telemetry circuit 300 advantageously allows intracardiac electrograms and status information relating to the operation of pacer/ICD 10 (as contained in the microcontroller 260 or memory 294) to be sent to the external device $3_{02}$ through an established communication link 304. In the preferred embodiment, pacer/ICD 10 further includes an activity sensor 308, commonly referred to as a "rate-responsive" sensor because it is typically used to adjust pacing stimulation rate according to the exercise state of the patient. However, sensor 308 may further be used to detect changes in cardiac output, changes in the physiological condition of the heart, or diurnal changes in activity (e.g., detecting sleep and wake states). Accordingly, the microcontroller 260 responds by adjusting the various pacing parameters (such as rate, AV Delay, V-V Delay, etc.) at which the atrial and ventricular pulse generators, 270 and 272, generate stimulation pulses. While shown as being included within pacer/ICD 10, it is to be understood that the physiologic sensor 308 may also be external to pacer/ICD 10, yet still be implanted within or carried by the patient. A common type of rate responsive sensor is an activity sensor, such as an accelerometer or a piezoelectric crystal, which is mounted within the housing 240 of pacer/ICD 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient.

The pacer/ICD additionally includes a battery 310, which provides operating power to all of the circuits shown in FIG. 6. The battery 310 may vary depending on the capabilities of pacer/ICD 10. If the system only provides low voltage therapy, a lithium iodine or lithium copper fluoride cell may be utilized. For pacer/ICD 10, which employs shocking therapy, the battery 310 must be capable of operating at low current drains for long periods, and then be capable of providing high-current pulses (for capacitor charging) when the patient requires a shock pulse. The battery 310 must also have a predictable discharge characteristic so that elective replacement time can be detected. Accordingly, pacer/ICD 10 is preferably capable of high voltage therapy and employs lithium/silver vanadium oxide batteries, as is true for most (if not all) current devices. As further shown in FIG. 6, pacer/ICD 10 is shown as having an impedance measuring circuit 312 which is enabled by the microcontroller 260 via a control signal 314. Here, thoracic impedance is primarily detected for use in tracking thoracic respiratory oscillations and tracking pulmonary edema. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 274 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 260 further controls a shocking circuit 316 by way of a control signal 318. The shocking circuit 316 generates shocking pulses of low (up to 0.5 joules), moderate (0.5-10 joules) or high energy (11 to 40 joules), as controlled by the microcontroller 260. Such shocking pulses are applied to the heart of the patient through at least two shocking electrodes, and as shown in this embodiment, selected from the left atrial coil electrode 228, the RV coil electrode 236, and/or the SVC coil electrode 238. The housing 240 may act as an active electrode in combination with the RV electrode 236, or as part of a split electrical vector using the SVC coil electrode 238 or the left atrial coil electrode 228 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 260 is capable of controlling the synchronous or asynchronous delivery of the shocking pulses.

Microcontroller 260 also includes the following components directed to calibrating blood $SO_2$ sensor 14. A patient activity detection unit 301 tracks patient activity based, for example, on signals received from sensor 308. A respiration rate detection unit 303 tracks respiration rate based on cyclic variations in signals received from impedance circuit 312. A pulmonary edema detection unit 305 tracks the degree of pulmonary edema in the patient based on averaged (i.e. DC) signals received from impedance circuit 312. A blood $SO_2$ sensor calibration unit 307 operates to calibrate voltage values received from sensor 14, using techniques described above in connection with FIGS. 2-4. Note that, although these various components are shown as being sub-components of the microcontroller, some or all may be implemented separately from the microcontroller. Depending upon the implementation, the various components of the microcontroller may be separate software modules. The modules may be combined so as to permit a single module to perform multiple functions.

What have been described are various systems and methods for calibrating a blood $SO_2$ sensor using a pacemaker, ICD or other implantable medical device. However, principles of the invention may be exploiting using other implantable systems or in accordance with other techniques. Thus, while the invention has been described with reference to particular exemplary embodiments, modifications can be made thereto without departing from the spirit and scope of the invention.

What is claimed is:

1. A method for calibrating an implantable blood oxygen saturation ($SO_2$) sensor for use with an implantable medical system, the method comprising:

storing a baseline blood oxygen saturation level measured by the blood oxygen saturation sensor;

detecting values representative of respiration rate, patient activity and degree of pulmonary edema within patient;

identifying a period of time when the detected values are each within predetermined acceptable ranges;

determining a calibration factor as a function of the baseline blood oxygen saturation level, the calibration factor being determined during the period of time when the detected values are each within predetermined acceptable ranges; and calibrating the oxygen saturation sensor using the calibration factor.

2. The method of claim 1 wherein the predetermined acceptable ranges specify one or more of a normal respiration rate, a minimal level of activity and a minimal degree of pulmonary edema.

3. The method of claim 2 wherein the implantable system includes a thoracic impedance sensor and wherein detecting respiration rate comprises:
  detecting periodic changes in thoracic impedance using the thoracic impedance sensor; and
  deriving patient respiration rate from the periodic changes in thoracic impedance.

4. The method of claim 3 wherein identifying a period of time when respiration rate is normal includes:
  comparing the respiration rate against predetermined upper and lower threshold values representative of the bounds of normal respiration; and
  determining that the respiration rate is normal if the respiration rate is between the upper and lower threshold values.

5. The method of claim 2 wherein the implantable system includes an activity sensor and wherein a patient activity level is detected using the activity sensor.

6. The method of claim 5 wherein identifying a period of time when activity is minimal includes:
  comparing the patient activity level against a predetermined activity threshold value; and
  determining that the patient activity is minimal if the activity level is below the activity threshold value.

7. The method of claim 2 wherein the implantable system includes a thoracic impedance sensor and wherein detecting the degree of pulmonary edema comprises:
  measuring trans-thoracic impedance value during expiration using the thoracic impedance sensor; and
  determining a degree of pulmonary edema based on the measured trans-thoracic impedance.

8. The method of claim 7 wherein identifying a period of time when pulmonary edema is minimal includes:
  comparing the measured trans-thoracic impedance value against a predetermined trans-thoracic threshold value; and
  determining that the degree of pulmonary edema is minimal if the average thoracic impedance value is above the trans-thoracic threshold value.

9. The method of claim 1 wherein determining a calibration factor during the period of time includes:
  measuring a new oxygen saturation value using the oxygen saturation sensor;
  retrieving a stored oxygen saturation value obtained during a previous period of time when the detected values were each within predetermined acceptable ranges; and
  calculating the calibration factor as the ratio of the newly measured oxygen saturation value and the stored baseline oxygen saturation value.

10. The method of claim 9 including the additional step of replacing the stored oxygen saturation value with the newly measured oxygen saturation value.

11. The method of claim 9 wherein calibrating the oxygen saturation sensor using the calibration factor includes the step of multiplying all new values sensed using the oxygen saturation sensor by the calibration factor.

12. The method of claim 1 including the additional step of tracking changes in the calibration factor over time.

13. The method of claim 12 including the additional step of identifying any trends in the changes in the calibration factor over time.

14. A system for calibrating an implantable blood oxygen saturation ($SO_2$) sensor for use with an implantable medical system, the system comprising:
  memory for storing a baseline blood oxygen saturation level measured by the blood oxygen saturation sensor;
  a parameter detection system operative to detect values representative of respiration rate, patient activity and degree of pulmonary edema within patient; and
  an oxygen saturation sensor calibration system operative to identify a period of time when the detected values are each within predetermined acceptable ranges, to determine a calibration factor as a function of the baseline blood oxygen saturation level, the calibration factor being determined during the period of time when the detected values are each within predetermined acceptable ranges, and to calibrate the oxygen saturation sensor using the calibration factor.

15. A system for calibrating an implantable blood oxygen saturation ($SO_2$) sensor for use with an implantable medical system, the system comprising:
  means for storing a baseline blood oxygen saturation level measured by the blood oxygen saturation sensor;
  means for detecting patient respiration rate;
  means for detecting patient activity;
  means for detecting a degree of pulmonary edema within the patient;
  means for identifying a period of time when respiration rate is normal, activity is minimal and pulmonary edema is minimal; and
  means for calibrating the oxygen saturation sensor using a calibration factor determined as a function of the baseline blood oxygen saturation level, the calibration factor being determined during the period of time when respiration rate is normal, activity is minimal and pulmonary edema is minimal.

\* \* \* \* \*